United States Patent [19]

Miklusek

[11] Patent Number: 5,443,460
[45] Date of Patent: Aug. 22, 1995

[54] NON-KINKING TUBING ADAPTOR FOR INTRAVENOUS CATHETER AND ASSOCIATED FLEXIBLE TUBING

[76] Inventor: John M. Miklusek, 135 S. Marshall St., York, Pa. 17402

[21] Appl. No.: 75,221

[22] Filed: Jun. 10, 1993

[51] Int. Cl.⁶ ............................................. A61M 25/00
[52] U.S. Cl. .................................. 604/282; 604/180; 128/DIG. 26
[58] Field of Search ............... 604/174, 180, 280, 282, 604/283, 905; 128/DIG. 6, DIG. 26

[56] References Cited

U.S. PATENT DOCUMENTS

| | | | |
|---|---|---|---|
| 3,059,645 | 10/1962 | Hasbrouck et al. | 128/346 |
| 3,853,126 | 12/1974 | Schulte | 604/175 |
| 3,942,528 | 3/1976 | Loeser | 604/174 |
| 4,261,363 | 4/1981 | Russo | 604/174 |
| 4,606,735 | 8/1986 | Wilder et al. | 128/DIG. 26 |
| 4,642,091 | 2/1987 | Richmond | 128/DIG. 26 |
| 4,895,561 | 1/1990 | Mahurkar | 604/174 |
| 4,976,698 | 12/1990 | Stokley |  |
| 5,053,023 | 10/1991 | Martin | 604/282 |
| 5,116,324 | 5/1992 | Brierley et al. | 604/174 |
| 5,147,320 | 9/1992 | Reynolds et al. | 604/174 |
| 5,156,592 | 10/1992 | Martin et al. | 604/282 |

OTHER PUBLICATIONS

Catalog p. R-3-Baxter Healthcare Corporation Interlink TM Catheter Extension Sets-effective date Feb. 17, 1992.

*Primary Examiner*—C. Fred Rosenbaum
*Assistant Examiner*—Chalin Smith
*Attorney, Agent, or Firm*—Woodcock Washburn Kurtz, Mackiewicz & Norris

[57] ABSTRACT

A non-kinking tubing adaptor for an intravenous catheter and associated flexible tubing including a rigid tube having a J-shaped configuration, the short end of the J-shaped tube being constructed for connection to an intravenous catheter and the long end of the J-shaped tube being constructed for connection to a flexible intravenous tubing.

8 Claims, 1 Drawing Sheet

NON-KINKING TUBING ADAPTOR FOR INTRAVENOUS CATHETER AND ASSOCIATED FLEXIBLE TUBING

FIELD OF THE INVENTION

The present invention generally relates to an intravenous catheter and associated flexible tubing for use with a patient and more particularly to a non-kinking tubing adaptor for an intravenous catheter and associate flexible tubing.

BACKGROUND OF THE INVENTION

Intravenous (IV) catheters are well known in the medical field and are used for a wide variety of applications including hydration and administration of medications, feeding and blood transfusions. A typical intravenous infusion system includes a catheter for penetrating the skin and underlining vein of the patient usually in the patient's forearm or hand, a source of fluid and flexible plastic tubing interconnecting the source of fluid and the intravenous catheter. It is common practice to secure the intravenous catheter and a portion of its associated flexible tubing to the limb of the patient to minimize movement of the catheter relative to the limb. This is normally accomplished with adhesive tape. A loop is normally formed in the end of the flexible tubing that connects to the intravenous catheter. It is important that the loop be secured to the limb of the patient in a manner so as to avoid kinking the flexible tubing which would result in a shut-off of the fluid through the tubing. In the past various arrangements have been proposed for securing the catheter and tubing to the patient so as to avoid kinking and unnecessary movement. Examples of various prior art devices are disclosed in U.S. Pat. Nos. 3,059,645, 3,942,528, 4,976,698 and 5,116,324. Such prior art devices require separate apparatus for maintaining the "U" in the flexible tubing. While such prior art devices appear to be successful in maintaining the "U" in the flexible tubing, they have left something to be desired in regard to bulk and comfort of the patient.

It will be understood that the majority of IV placements are made around the areas of the wrist and the back of the hand of the patient. The obtrusiveness of the tubing loop or any separate for maintaining the "U" in the flexible tubing makes the IV placement quite vulnerable due to random movements of the hand and arm. Displacement of the IV catheter can be quite serious, especially when a patient is very ill and available veins for placement of the catheter are at a minimum. It would be desirable to provide the flexible tubing with a rigid U-shaped section for connection to an intravenous catheter. This would eliminate the bulk of any extra apparatus, permit the use of a smaller U-shaped section and still permit the intravenous catheter and associated flexible tubing to be secured to the patient's limb with adhesive tape for a light weight connection.

SUMMARY OF THE INVENTION

In accordance with the present invention there is provided a non-kinking tubing adaptor for an intravenous catheter and associated flexible tubing. The adaptor comprises a rigid tube having a pair of straight tube connections interconnected by a U-shaped tube section. An adaptor is positioned on the free end of one of the straight sections for connection to an intravenous catheter and the end of the other straight section remote from the U-shaped section is adapted for connection to a flexible intravenous tubing. In the preferred form of the invention the rigid tube is J-shaped with the short section of the "J" being provided with an adaptor for connection to an intravenous catheter. The long leg of the J-shaped adaptor may be provided with an adaptor for connection to the flexible intravenous tubing or the flexible intravenous tubing may be bonded directly to the long leg of the J-shaped adaptor.

DESCRIPTION OF THE PREFERRED EMBODIMENT

Figures 1, 2:
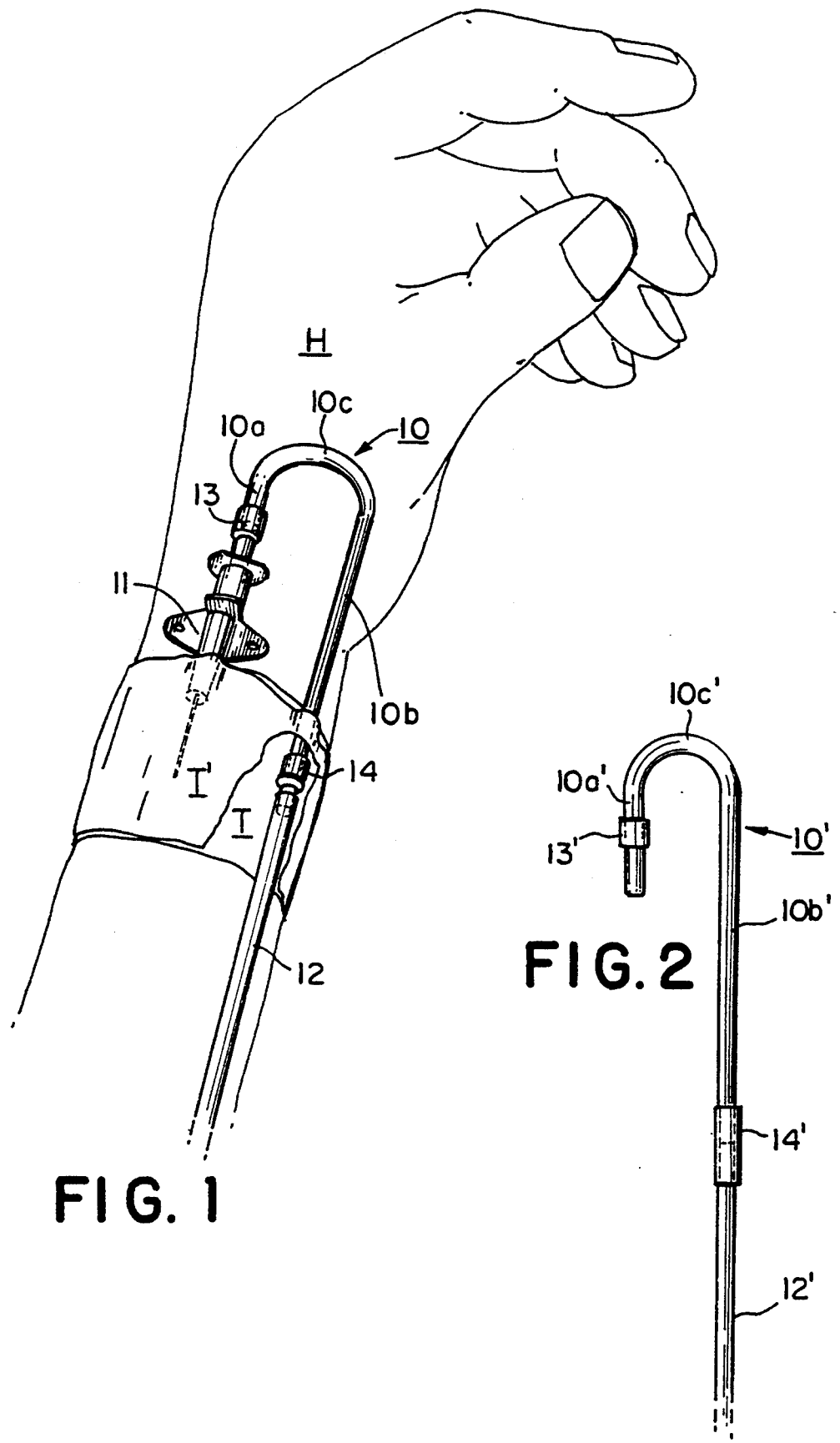
FIG. 1 is a perspective view of a non-kinking tubing adaptor for an intravenous catheter and associated flexible tubing in accordance with the present invention shown in position on an intravenous site on the forearm of a patient.
FIG. 2 is a modification of the non-kinking tubing adaptor in accordance with the present invention.

Referring to FIG. 1 there is illustrated an intravenous system embodying the present invention. The system includes the novel non-kinking tubing adaptor 10 which interconnects the intravenous catheter 11 and a flexible plastic IV tubing 12. The non-kinking tubing adaptor 10 comprises a rigid tube, preferably plastic, having a pair of straight sections 10a and 10b interconnected by a U-shaped section 10c. As may be seen in FIG. 1 the rigid tube is preferably J-shaped, the straight tube section 10a being shorter than the other straight tube section 10b. As may be seen from FIG. 1 the term "tube" is used herein in accordance with its ordinary dictionary definition, namely a hollow elongated cylindrical body. The tube section 10a is provided with a male connector 13 for insertion in the female connector portion of the intravenous catheter 11. The other leg 10b of the rigid tube 10 is provided with a female connector 14 for receiving an adaptor or directly connected to the flexible IV tubing 12. The flexible IV tubing 12 is connected to a source of intravenous fluid, not shown.

In practice the intravenous catheter 11 is maintained in place on the patient's forearm or hand by a piece of adhesive tape T. After the connector 13 of the rigid J-shaped tube 10 has been inserted in the intravenous catheter, the tube 10 is held in place on the patient's arm by a second piece of adhesive tape T' applied over the first piece of tape T. With this arrangement, the required loop in the intravenous tubing system will be maintained by virtue of the rigid adaptor 10 and the complete system is readily maintained in position on the patient's arm by the use of adhesive tape. This arrangement provides a simple light weight intravenous system which permits the use of a smaller loop and is comfortable for the patient but at the same time ensures that the loop in the intravenous tubing system will remain unkinked.

Referring to FIG. 2 there is shown another non-kinking tubing adaptor 10' embodying the present invention. In this embodiment, the adaptor 10' is a rigid tube and is similar to the adaptor 10. The adaptor 10' comprises a pair of straight sections 10a' and 10b' interconnected by a U-shaped section 10c'. A connector 13' is positioned on the short leg 10a' of the J-shaped rigid tube. The long leg 10b' of the J-shaped tube instead of being provided with a detachable connector is permanently connected as by bonding to the end of the flexible tubing 12 with a bonding sleeve 14'.

The tubing adaptor's 10 and 10' may be made from any suitable plastic material which may be formed as a rigid tube. The connectors 13 and 14 are conventional press fitting connectors used in intravenous systems. The intravenous tubing 12 is also conventional plastic tubing used in intravenous systems.

From the foregoing it will be seen that the novel tubing adaptor of the present invention not only eliminates the kinking normally inherent in flexible tubing intravenous systems but by reason of its rigid tube construction it permits the use of a smaller loop. A smaller loop is particularly desirable with regard to infants and children and the smallness in size minimizes the vulnerability of displacement of the IV due to random movements of the hand and arm by the patient. As an example of size, the dimension across the U-shaped portion 10c may be as small a $\frac{3}{4}"$. The dimension of the short leg 10a measured from the end of the adaptor 13 to the top of the U-shaped portion 10c may be in the order of 1" and the length of the longer leg 10b measured from the end of the adaptor 14 to the top edge of the U-shaped portion 10c may be in the order of 2". An adaptor 10 with these dimensions is large enough to be firmly secured to the limb of the patient with adhesive tape but is also small enough to provide for comfort of the patient.

While a preferred embodiment of the invention has been described and illustrated, it is to be understood that further modification thereof will be made within the scope of the appended claims without departing from the spirit of the invention.

What is claimed is:

1. In an intravenous system for supplying fluid from a fluid source through a flexible intravenous tubing to an intravenous catheter, the combination comprising a non-kinking tubing adaptor connected between the flexible intravenous tubing and the intravenous catheter, said adaptor comprising a rigid one-piece tubing having a pair of straight tube sections interconnected by a U-shaped tube section, all of said sections being rigid throughout the length of said tubing forming a hollow elongated cylindrical body, a connector on the free end of one of said straight sections constructed for connection to the intravenous catheter and the end of the other straight section remote from said U-shaped section being constructed for connection to the flexible intravenous tubing.

2. In an intravenous system having a non-kinking tubing adaptor according to claim 1 wherein said rigid tube is J-shaped.

3. In an intravenous system having a non-kinking tubing adaptor according to claim 1 wherein the first named straight tube section is shorter than the second named straight tube section.

4. In an intravenous system having a non-kinking tubing adaptor according to claim 1 wherein the second named straight tube section is provided with a connector for connection to the flexible intravenous tubing.

5. In an intravenous system having a non-kinking tubing adaptor according to claim 1 wherein said end of the other straight tube section remote from said U-shaped section is integral with the flexible intravenous tubing.

6. In an intravenous system having a non-kinking tubing according to claim 1 wherein said end of the other straight tube section remote from said U-shaped section is bonded to one end of the flexible intravenous tubing to provide a continuous flow path to the intravenous catheter.

7. In an intravenous system having a non-kinking tubing adaptor according to claim 1 wherein said rigid tube is plastic.

8. In an intravenous system for supplying fluid from a fluid source through a flexible intravenous tubing to an intravenous catheter, the combination comprising a non-kinking tubing adaptor connected between the flexible intravenous tubing and the intravenous catheter, said adaptor comprising a rigid one piece tube having a J-shaped configuration, the short end of the J-shaped tube being constructed for connection to the intravenous catheter and the long end of the J-shaped tube being constructed for connection to the flexible intravenous tubing, said J-shaped tube being rigid throughout the length thereof forming a hollow elongated cylindrical body.

* * * * *